US005696152A

United States Patent [19]

Southard

[11] Patent Number: 5,696,152
[45] Date of Patent: Dec. 9, 1997

[54] TAXOL COMPOSITION FOR USE AS ORGAN PRESERVATION AND CARDIOPLEGIC AGENTS

[75] Inventor: James H. Southard, Madison, Wis.

[73] Assignee: Wisconsin Alumni Research Foundation, Madison, Wis.

[21] Appl. No.: 646,055

[22] Filed: May 7, 1996

[51] Int. Cl.$^6$ .............................. A01N 43/02; A01N 37/00; A01N 1/02
[52] U.S. Cl. ............................. 514/449; 514/510; 435/1; 435/1.1; 435/1.2
[58] Field of Search ........................ 514/449, 510, 514/832; 435/1, 1.1, 1.2, 283

[56] References Cited

U.S. PATENT DOCUMENTS

| | | | |
|---|---|---|---|
| 4,798,824 | 1/1989 | Belzer et al. | 514/60 |
| 4,873,230 | 10/1989 | Belzer et al. | 514/60 |
| 4,879,283 | 11/1989 | Belzer et al. | 514/60 |
| 5,145,771 | 9/1992 | Lemasters et al. | 435/1 |
| 5,344,775 | 9/1994 | Smith | 435/240.51 |
| 5,352,805 | 10/1994 | Kingston et al. | 549/10 |
| 5,370,989 | 12/1994 | Stern et al. | 435/1 |
| 5,405,742 | 4/1995 | Taylor | 435/1 |
| 5,407,683 | 4/1995 | Shively | 424/439 |
| 5,407,793 | 4/1995 | Nido et al. | 435/1 |
| 5,422,364 | 6/1995 | Nicolaou et al. | 514/449 |
| 5,424,073 | 6/1995 | Rahman et al. | 424/450 |
| 5,451,392 | 9/1995 | Strobel et al. | 424/181 |
| 5,565,317 | 10/1996 | Dohi et al. | 435/1.2 |

FOREIGN PATENT DOCUMENTS

| | | |
|---|---|---|
| WO 95/05076 | 2/1995 | WIPO . |
| WO95/20582 | 8/1995 | WIPO . |

OTHER PUBLICATIONS

Paul Jenkins, Taxol Branches Out, Chemistry in Britain, vol. 32, No. 11, pp. 43–45, Nov. 1996.

*Primary Examiner*—Cecilia J. Tsang
*Assistant Examiner*—Jennifer Harle
*Attorney, Agent, or Firm*—DeWitt Ross & Stevens S.C.

[57] ABSTRACT

A composition containing taxol for the ex vivo preservation or perfusion of organs for implantation in a subject requiring such implantation, or for cardioplegia, is disclosed.

21 Claims, 1 Drawing Sheet

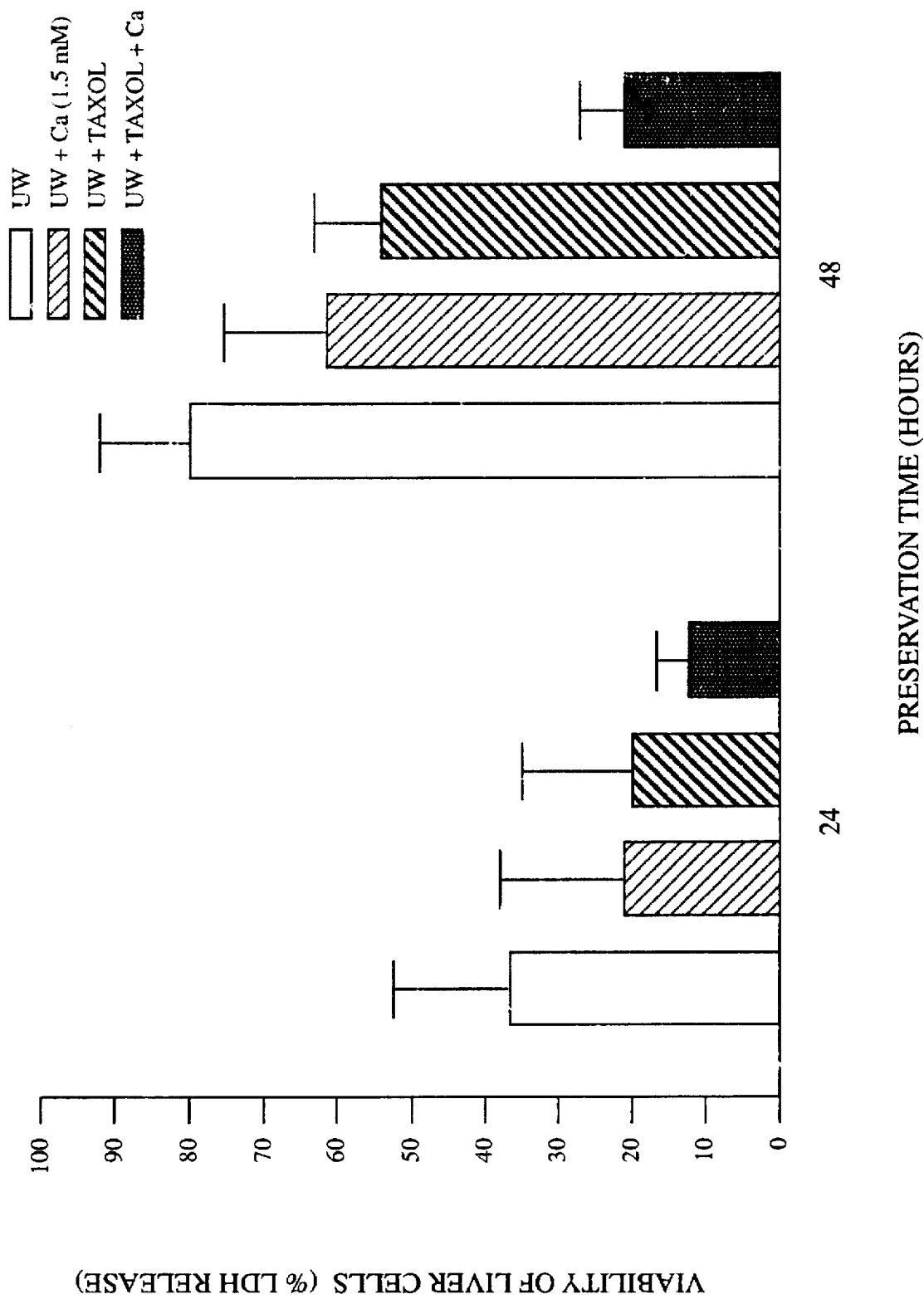

TAXOL COMPOSITION FOR USE AS ORGAN PRESERVATION AND CARDIOPLEGIC AGENTS

FIELD OF THE INVENTION

The present invention relates to compositions for the ex vivo preservation and storage of organs prior to implantation of an organ into a subject in need of such implantation. The compositions also double as effective cardioplegic agents for the reversible cessation of a beating heart during surgical procedures. Specifically, the present invention relates to organ preservation and storage solutions and cardioplegic agents which include taxol.

DESCRIPTION OF THE PRIOR ART

The last two decades have seen organ transplantation proceed from a rare research and experimental procedure into an established clinical therapy for the end-stage treatment of various terminal malfunctions of the heart, liver, pancreas, lung, intestine, and kidney. Progress in the science of organ transplantation has evolved to the point that such procedures are now rarely deemed to be newsworthy.

As organ transplantation has become an accepted clinical practice, however, the need for extending the viable ex vivo preservation and storage of organs for implantation has become acute. Due to the success of surgeons in perfecting organ transplantation protocols, and the widespread use of immuno-suppressant drugs which minimize the host's rejection of the implanted organ, waiting lists for organ transplant procedures have grown enormously. This has caused a critical shortage of viable organs to be transplanted.

Minimizing the wastage of precious organs for transplantation is therefore critical. Such waste often occurs due to the amount of time required to match the tissue type of the organ to the tissue type of the recipient, and also the time required to physically transport the stored organ to the patient's location. Due to the present inability to store excised organs for a prolonged period of time, the ex vivo organ often becomes nonviable before a suitable match can be established. By prolonging the viable storage time, such waste can be significantly minimized by providing sufficient time for the necessary tissue match and transportation to occur.

Because organ transplantation has been a very active field, the prior art contains several references describing organ preservation and perfusion solutions for the ex vivo storage of organs prior to their transplantation. For instance, the work of the present inventor, as embodied in U.S. Pat. Nos. 4,798,824; 4,873,230; and 4,879,283 to Belzer and Southard, describes an organ preservation solution which has come to be referred to as the "UW Solution." (The solution was developed at the University of Wisconsin, Madison.) The UW Solution is sold under the trademark VIASPAN by the Du Pont de Nemours Company, Wilmington, Del. A related solution is marketed by Geneva Labs, Elkhorn, Wis., as a perfusion solution under the trademark BELZER'S PERFUSION SOLUTION. Each of the above patents is incorporated herein by reference in it entirety.

The Belzer and Southard patents describe an organ preservation solution which contains hydroxy ethyl starch. In one embodiment of the solution, the hydroxy ethyl starch is substantially free of ethylene glycol, ethylene chlorohydrin, and acetone. As noted in the '283 patent, the solution described therein provides 72-hour preservation for the pancreas, 48-hour preservation for the kidney, and at least 24-hour preservation for the liver.

Lemasters et al. describe an organ preservation solution popularly referred to as the "Carolina Solution." This solution is described in U.S. Pat. No. 5,145,771 and PCT Publication WO 95/05076, both of which are incorporated by reference herein in their entirety. The solution described in these two references can be used either as a rinsing solution to prevent re-perfusion injury, or as a storage solution, per se. The solution is described as having an operating temperature range of from 0° C. to 37° C. The solution is further described as containing a balance of sodium, calcium, and potassium chloride salts; magnesium sulfate, monopotassium phosphate, and antioxidant such as allopurinol, vasodilators, and an ATP energy source such as glucose or fructose. Similar to the UW Solution, the Carolina Solution may also include modified hydroxy ethyl starch to provide oncotic support against interstitial edema.

U.S. Pat. No. 5,370,989 to Stern et al., assigned to Columbia University, describes an organ preservation solution in which the use of sodium ions, chloride ions, and calcium ions is specifically avoided. Of particular interest in this reference is the use of an analog of cyclic adenosine monophosphate (cAMP), specifically, dibutyryl cAMP. Other ingredients included in the solution described by the Stern et al. patent include glucose, magnesium sulfate, monopotassium phosphate, dextran, potassium gluconate, BHA, BHT, N-acetycystine, adenosine, nitroglycerine, a calcium blocker such as verapamil, heparin, and cefazolin. This patent specifically notes that the intended use of the solution is for the preservation of heart tissue. The patent does note that the same solution may, however, be used successfully to preserve livers, pancreases, kidneys, lungs, and other organs.

A related type of solution is described by Taylor in U.S. Pat. No. 5,405,742. This patent describes a hypothermic blood substitute which can be used to replace the blood in a euthermic subject. In these procedures, the patient's body temperature is lowered to minimize damage to the subject's brain and vital organs. By reducing the temperature well below that normally maintained by the patient, the patient's metabolic rate is significantly lowered. This, in turn, decreases the demands for oxygen and glucose of the tissues and organs of the patient. Here, rather than explanting the organ from a donor subject, the blood of the donor is purged and replaced with the hypothermic blood substitute. This solution is described in the Taylor reference as containing an aqueous solution of electrolytes including potassium ions, sodium ions, magnesium ions, and calcium ions; a macromolecular oncotic agent, preferably a polysaccharide such as dextran 40; a biological pH buffer, at least one simple sugar, mannitol, an impermeant anion, adenosine, and, optionally, glutathione. The solution may also contain a calcium blocker such as nicardipine. This reference describes successfully purging the blood of a test animal (a dog) for more than three hours, followed by reintroduction of the blood with complete recovery and recuperation of the test animal.

As noted by Stern et al., cardioplegic agents are used to stop the heart from beating during cardiac surgery. The principles of organ preservation apply equally to cardioplegic agents, and therefore these two types of materials are related. During open heart surgical procedures, the patient's circulatory system is shunted to an external heart-lung machine which circulates and oxygenates the patient's blood. A cardioplegic agent is then contacted with the patient's heart to cease its beating. In this fashion, the patient's heart is reversibly stopped so that the surgeons may complete the required procedure, such as coronary artery bypass surgery. In excess of 200,000 such procedures are performed annually in the United States alone.

The present inventors have found that the inclusion of taxol in an organ preservation or perfusion solution, or in a cardioplegic agent, prolongs the effective storage time which can be achieved using the solution.

Taxol is a member of the taxane family of diturpenes. The structure of taxol and its systematic name are given below:

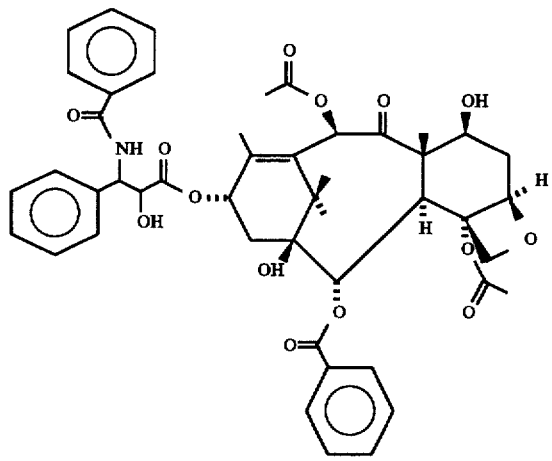

TAXOL=(2aR-(2aα, 4β, 4αβ, 6β, 9α(βR*,βS*),11α, 12α, 12aα, 1-2bα)) -β-(Benzoylamino-α-hydroxybenzenepropanoic acid6,12b-bis(acetyloxy)-12-benzoyloxy) -2a,3,4,4a,5,6,9,10,11,12,12a,12b,- dodecahydro-4,11-dihydroxy-4a,8,13,13-tetramethyl-5-oxo-7,11-methano-1H-cyclodeca(3,4)benz(1,2-b)oxet-9-yl ester.

Taxol was first isolated from the bark of the Pacific yew tree, *Taxus breviofoila*. Taxol has known anti-leukemic and anti-tumor activity and has been the subject of intense study as a chemotherapeutic agent in the treatment of cancer. An excellent discussion of taxol and a large number of taxol derivatives can be found in PCT published application WO 95/20582, assigned to the Upjohn Company, Kalamazoo, Mich. The contents of this patent publication is incorporated by reference herein in its entirety.

The pharmaceutical use of taxol, however, suffers from two major disadvantages. The first is that taxol occurs quite rarely in nature. Moreover, the Pacific yew tree from which taxol is isolated is relatively rare, grows very slowly, and yields an extremely small amount of taxol per tree. This makes harvesting natural taxol a practical impossibility.

The second drawback to the use of taxol is its extremely limited aqueous solubility. For instance, Shively, U.S. Pat. No. 5,407,683, describes an oil-based solution of taxol or a tumor-active analog of taxol. Due to the water-insolubility of taxol, the taxol is first dissolved within an oil, and the oil-based taxol solution is then used in the formation of an oil-in-water emulsion. The oil-in-water emulsion is then used as a delivery vehicle in the administration of taxol.

The Shively patent also notes that taxol has conventionally been administered in formulations using cremophors. Taxol has a relatively high solubility in these polyoxyethylated castor oils, but several cremophors themselves are sufficiently toxic to preclude their use as pharmaceutically-acceptable carriers. Also, taxol is insufficiently soluble in soybean oil to use this vehicle in the parenteral administration of taxol. Shively describes dissolving taxol in oils from marine organisms which have a dipole moment of between about 0.5 Debyes and about 2.0 Debyes. However, no mention is made in this reference of the use of taxol in an organ preservation or cardioplegic composition. The same can be said for all of the references described herein.

Kingston et al., U.S. Pat. No. 5,352,805, describes derivatives of taxol which have increased water solubility. Specifically, Kingston et al. describe sulfonated 2'-acryloyltaxol and sulfonated 2'-O-acyl acid taxol derivatives. As compared to taxol itself, these derivatives have improved water solubility and increased stability. Additionally, the bioactivity of the original taxol is maintained. The Kingston et al. reference is incorporated herein in its entirety for its teaching of water soluble derivatives of taxol.

Nicolaou et al., U.S. Pat. No. 5,422,364, also describes taxol derivatives which have increased water solubility as compared to taxol itself. Here, an alkaline-sensitive pro-taxol is described. The pro-taxol compositions include 2' and 7-O-ester derivatives of taxol, as well as 2' and 7-O-carbonate derivatives. At physiological pH, these pro-taxols are hydrolyzed to render the native taxol structure. The Nicolaou et al. reference is also incorporated herein by reference in its entirety.

Liposome-encapsulated taxol is described in U.S. Pat. No. 5,424,073 to Rahman et al., incorporated herein by reference in its entirety. Rather than altering the substituents on the taxol skeleton, this reference describes encapsulating native taxol within a liposome. This ameliorates many of the solubility problems of taxol. Additionally, the authors note that liposome encapsulation improves taxol stability, while lessening the chance of anaphylactoid reactions and cardio toxicity.

The production of taxol is described in references to Smith (U.S. Pat. No. 5,344,775) and Strobel et al. (U.S. Pat. No. 5,451,392). The Smith patent describes the synthesis of a wide range of taxanes in a culture of cells taken from the pseudocallus of Pacific yew trees. The various taxanes, including taxol, can be isolated from pseudocallus cells which have been cultured on a support culture medium.

The Strobel et al. reference describes the formation of taxol by contacting a sterilized yew tree stock with a reactor solution. The solution contains a reducing agent, an energy source, a buffer to maintain the pH within a defined range, a steroid inhibitor, and a taxol precursor. The natural metabolic action of the yew tree stock functions to synthesize the formation of taxol from the taxol precursor. Additionally, a radio-labelled precursor may be included in the reactor solution to yield a radio-labelled taxol.

None of the above references, taken alone, or in any combination, is seen as describing the use of taxol in an organ preservation solution.

SUMMARY OF THE INVENTION

In light of the above discussion, the present invention is drawn to a composition for the ex vivo preservation and storage of organs intended for implantation into a subject requiring such implantation, the composition comprising a physiologically-acceptable ex vivo storage solution containing taxol and calcium.

The present invention is further directed to a composition for the ex vivo preservation and storage of organs intended for implantation into a subject requiring such implantation which comprises a physiologically-acceptable ex vivo storage solution having a solution osmolality of about 320 mOsm/liter and including taxol, calcium, and a lactobionate salt. The solution also contains about 3 to 8 weight percent hydroxy ethyl starch having a molecular weight of from about 150,000 to about 350,000 Daltons, and wherein the starch is substantially free of ethylene glycol, ethylene chlorohydrin, sodium chloride, and acetone.

The composition according to the present invention may also contain further ingredients, among them: about 5 weight percent hydroxy ethyl starch having a molecular of from about 200,000 to about 300,000 Daltons, from about 1 to about 100 nM taxol, about 25 mM potassium phosphate, about 3 mM glutathione, about 5 mM adenosine, about 10 mM glucose, about 10 mM HEPES buffer, about 5 mM magnesium gluconate, about 1.5 mM calcium chloride, about 105 mM sodium gluconate, 200,000 units penicillin, 40 units insulin, and wherein the solution has a pH of from 7.4 to 7.5.

The present invention is also drawn to improvements in ex vivo storage solutions and cardioplegic agents. In particular, in a solution for the ex vivo preservation and storage of organs intended for implantation into a subject requiring such implantation, the present invention is drawn to the improvement comprising adding taxol and calcium to the ex vivo organ preservation and storage solution. Preferably, the taxol is present in an amount ranging from about 1 to about 100 nM, and the calcium is present in an amount of from about 0.5 to about 1.5 µM.

In a similar vein, the present invention is also drawn to a cardioplegic composition which comprises a physiologically-acceptable cardioplegic solution containing taxol and calcium.

It is a principal aim of the present invention to provide a solution for the ex vivo storage and preservation of organs which contains taxol or one or more taxol derivatives.

Another aim of the present invention is to provide an organ preservation solution containing taxol or a taxol derivative which extends the effective ex vivo storage period of explanted organs prior to transplantation into a subject requiring such transplantation.

Yet a further aim of the present invention is to provide an organ preservation and perfusion solution containing taxol or taxol derivatives which minimizes tissue damage to organs stored ex vivo prior to their transplantation.

A still further aim of the present invention is the effective use of taxol derivatives having increased water solubility in a solution for the ex vivo storage and maintenance of explanted organs prior to their transplantation into a subject requiring such transplantation.

Still another aim of the invention is to provide a cardioplegic agent containing taxol or one or more taxol derivatives.

A further aim of the present invention is to provide a cardioplegic agent containing taxol which has been modified to increase its aqueous solubility, as by incorporation in a liposome.

The principal advantage of the present organ preservation solution is that it extends the viable ex vivo storage time for organs to be transplanted, thereby minimizing wastage of the life-saving organs. Likewise, when used as a cardioplegic agent or perfusate, the present composition minimizes tissue damage upon resuscitation of the heart or re-perfusion of the stored organ.

These and other aims, objects, and advantages of the present invention will become apparent upon a complete reading of the Detailed Description, drawing FIGURES, and claims, below.

BRIEF DESCRIPTION OF THE DRAWING

The sole drawing FIGURE is a graph depicting the effect of taxol and calcium on the survival rate of rat hepatocytes stored for 24 hours and for 48 hours in the UW Solution. The Y-axis of the graph depicts the percentage of free LDH, which is a proportional measurement of hepatocellular necrosis. Consequently, LDH levels are inversely proportional to cell survival. A low level of LDH indicates a high level of cell survival. Plots are depicted for cell survival rate in the UW Solution alone, the UW Solution plus 1.5 mM $Ca^{++}$, the UW Solution plus taxol, and the UW Solution plus 1.5 mM $Ca^{++}$ plus taxol. The nominal concentration of taxol in the above solutions was approximately 100 µM.

DETAILED DESCRIPTION OF THE INVENTION

The present invention is an ex vivo organ preservation and perfusion solution and cardioplegic agent containing taxol or one or more taxol derivatives, and, preferably, calcium. For sake of clarity and brevity, the term "organ preservation solution" as used hereinbelow shall be deemed to be synonymous with "organ storage solution," "organ perfusion solution," and "cardioplegic agent." This convention does not limit the invention disclosed and claimed herein in any fashion, but is merely a means to concisely describe the preferred embodiment of the present invention. The following discussion applies with equal validity to all of these types of solutions.

Additionally, as used herein, the term "taxol" shall refer to taxol and any pharmaceutically-equivalent derivative or analog thereof. Included among such equivalents are physiologically-tolerated taxol salts, esters, alkyl and acyl derivatives, liposome-encapsulated derivatives, oil-in-water emulsions of taxol, and the like. Also encompassed within the term "taxol" as used herein are pharmaceutically-equivalent taxol derivatives which have been modified to have improved aqueous solubility as compared to native taxol.

It has been found, quite unexpectedly, that the inclusion of taxol and/or taxol derivatives in an ex vivo organ preservation solution significantly increases the amount of time an explanted organ can be successfully stored ex vivo prior to its transplantation into a subject requiring such transplantation. By providing for the prolonged storage of explanted organs, organ wastage can be minimized. It has also been found that the inclusion of taxol in a cardioplegic agent (i.e., an agent which, when applied to an in vivo beating heart, reversibly induces heartbeat cessation), lessens the extent of heart tissue injury upon resumption of the heartbeat.

As noted above, several basal organ preservation solutions, including the UW Solution, are known in the art. The present invention, an organ preservation solution including taxol and calcium, will perform with equal success using any type of basal organ preservation solution. It has been found that the addition of taxol to an organ preservation solution greatly increases its ability to maintain the viability of an explanted organ stored therein. It has further been found that the addition of calcium has a synergistic effect which increases the organ preservation capacity of a solution over time greater still.

While the organ preservation solution of the present invention will function with equal success using any type of basal organ preservation solution, two basal solutions, namely the UW Solution and Belzer's perfusion solution are preferred.

The UW basal solution contains hydroxy ethyl starch having a molecular of from about 200,000 to about 300,000 Daltons, potassium phosphate, glutathione, adenosine, potassium lactobionate, raffinose, magnesium sulfate, allopurinol, dexamethasone, penicillin, and insulin. Generally, the UW basal solution has a pH of from about 7.4 to 7.5.

Specifically, the preferred UW basal solution for use in the present invention contains about 5 weight percent hydroxy ethyl starch having a molecular of from about 200,000 to about 300,000 Daltons, about 25 mM potassium phosphate, about 3 mM glutathione, about 5 mM adenosine, about 100 mM potassium lactobionate, about 20 mM raffinose, about 5 mM magnesium sulfate, about 1.5 mM allopurinol, about 8 mg/l dexamethasone, about 200,000 units penicillin, and about 40 units insulin.

The Belzer basal perfusion solution also contains hydroxy ethyl starch, potassium phosphate, glutathione, adenosine, penicillin, and insulin, as in the UW basal solution. But, in contrast to the UW basal solution, the Belzer contains glucose, N-2-hydroxyethylpiperazine-N'-2-ethanesulfonic acid buffer (HEPES), magnesium gluconate, calcium chloride, and sodium gluconate. As in the UW basal solution, the Belzer basal solution preferably has a pH of from about 7.4 to about 7.5.

Specifically, the Belzer basal solution preferably contains about 5 weight percent hydroxy ethyl starch having a molecular of from about 200,000 to about 300,000 Daltons, about 25 mM potassium phosphate, about 3 mM glutathione, about 5 mM adenosine, about 10 mM glucose, about 10 mM HEPES buffer, about 5 mM magnesium gluconate, about 1.5 mM calcium chloride, about 105 mM sodium gluconate, about 200,000 units penicillin, and about 40 units insulin.

To the basal organ preservation solution is added taxol and calcium, preferably in the form of calcium chloride. In the case of the Belzer basal solution, which already contains an adequate supply of calcium ions, additional calcium need not be added. For basal solutions devoid of calcium, however, sufficient calcium should be added, preferably in the form of calcium chloride, to raise the calcium ion content to approximately 1.5 mM.

To introduce taxol, per se, into a solution, it is preferred that the taxol is first gently dissolved in dimethylsulfoxide (DMSO). Small amounts of the taxol-in-DMSO solution are then added, with gentle mixing, to the basal organ preservation solution. Because of the extreme aqueous insolubility of taxol, some taxol precipitating from solution is to be expected. Taxol and several taxol derivatives are available commercially from, for instance ICN Biomedicals, Inc., Aurora, Ohio, as well as other national and international suppliers.

Taxol should be added to the solution to give a nominal concentration of approximately 100 µM. At this level of saturation, the actual solution concentration of taxol in the basal solution ranges from approximately 1 to about 100 nM taxol. Even at this low concentration, taxol imparts a remarkably improved viable cold storage time for explanted organs.

It is preferred that the osmolality of the overall solution fall within the range of from approximately 300–350 mOsm/liter. It is most preferred that the solution have an osmolality of approximately 320 mOsm/l.

As illustrated by the Example, below, the presence of taxol and calcium in a basal organ preservation solution elicits a synergistic effect which is greater than the effects of either calcium alone or taxol alone.

EXAMPLE

The following Example is provided for illustrative purposes only, to provide a more complete understanding of the present invention. The Example does not limit the invention disclosed and claimed herein in any fashion.

All of the references described below are incorporated herein by reference in their entirety.

Sprague-Dawley rats weighing from 250 to 330 grams were used to isolate hepatocytes as described by Seglen (1976). In short, after excising the liver, the liver is perfused with collagenase at 37° C., which causes the liver tissue to be quantitatively converted into a suspension of individual cells.

The hepatocytes so isolated were then analyzed as described by Marsh et al (1990). Immediately after determining the viability of the isolate hepatocytes, cell samples were re-suspended in various cell preservation solution. Four groups of hepatocyte cold storage (4° C.) samples were assembled in duplicate. The first sample used the University of Wisconsin (UW) Solution, as described above, for the storage solution. The second sample used the UW Solution plus 1.5 mM calcium (in the form of calcium chloride) as the storage solution. The third sample used the UW Solution plus 100 µM taxol as the preservation solution. The fourth sample used the UW Solution plus 1.5 mM calcium (in the form of calcium chloride) and 100 µM taxol as the storage solution.

The suspended cells were then stored for 24 or 48 hours at 4° C. in an $O_2/CO_2$ atmosphere (95%/5%) in closed 125 ml polycarbonate Erlenmeyer flasks (25 ml of suspension per flask) with continuous shaking (orbital shaker, 90 RPM). Krebs Hanseleit buffer (KHB), a well known physiologically-buffered salt solution, was used to study the hepatocytes at normothermia (Marsh et al., 1990).

To prepare the solutions containing taxol, the taxol was first slowly dissolved in dimethylsulfoxide (DMSO). Small volumes of the resultant taxol-in-DMSO solution were then added to UW Solution to give a final nominal concentration of 100 µM. Calcium chloride was added directly to the UW Solution with gentle stirring.

To assess cell death, lactate dehydrogenase (LDH) was measured in the hepatocytes and in the supernate. LDH was analyzed using a commercially available kit from Sigma Chemical Company (St. Louis, Mo.), following the instructions provided with the kit.

The control hepatocytes were suspended in UW solution (4° C.) having a concentration of 5 mg protein/ml (as calculated by the biuret method). The cells were stored, without agitation, in centrifuge tubes. At the end of 24 of 48 hours of storage, the cells were sedimented by centrifugation (600×g), re-suspended in KHB (5 mg protein/ml) at 37° C., and incubated with shaking (90 to 100 rpm) in an atmosphere of room air. After 120 minutes of incubation, the cells were rapidly sedimented by centrifugation at 13,000×g for 30 seconds. Free LDH in the supernate was measured.

The sedimented cells were re-suspended in KHB and sonicated. Bound LDH from the sonicated cells was then measured.

The percentage of free LDH equals the amount of free LDH found in the cell supernate relative to the total amount of cellular LDH (free+bound).

Four different hepatocyte preparations were analyzed in duplicate. The results of the testing are depicted in the sole drawing FIGURE. The FIGURE shows the percentage of free LDH, which is proportional to cell death (inversely proportional to cell survival), for hepatocytes incubated in the UW solution alone, the UW solution plus 1.5 mM calcium, the UW solution plus taxol, and the UW solution plus taxol and calcium. As depicted in the FIGURE, the solutions rated, in order of maximum cell survival to minimum cell survival, as follows: UW solution plus taxol and calcium, the UW solution plus taxol, the UW solution plus 1.5 mM calcium, and the UW solution.

The present organ preservation solution and cardioplegic agent is not limited to the above-described preferred embodiment, but encompasses all such extensions and modifications thereof as fall within the scope of the attached claims.

What is claimed is:

1. A composition for the ex vivo preservation and storage of organs intended for implantation into a subject requiring such implantation, the composition comprising a physiologically-acceptable ex vivo organ preservation solution containing taxol and calcium.

2. The composition according to claim 1, wherein the physiologically-acceptable ex vivo organ preservation solution has an osmolality of from about 300 to about 350 mOsm/liter.

3. The composition according to claim 1, wherein the physiologically-acceptable ex vivo organ preservation solution further comprises about 3 to 8 weight percent hydroxyethyl starch having a molecular weight of from about 150,000 to about 350,000 Daltons; and wherein the starch is substantially free of ethylene glycol, ethylene chlorohydrin, sodium chloride, and acetone.

4. The composition according to claim 3, wherein the starch is substantially free of hydroxy ethyl starch having a molecular weight of less than about 50,000 Daltons.

5. The composition according to claim 3, wherein the physiologically-acceptable ex vivo organ preservation solution further comprises a lactobionate salt.

6. The composition according to claim 5, wherein the lactobionate salt is present in a concentration of about 100 millimolar.

7. The composition according to claim 3, further comprising at least one electrolyte in addition to calcium.

8. The composition according to claim 7, wherein the at least one electrolyte in addition to calcium is selected from the group consisting of sodium and potassium and is present in a concentration of from about 100 to about 125 millimolar.

9. The composition according to claim 3, further comprising raffinose.

10. The composition according to claim 1, wherein the taxol is present at a solution concentration of from about 1 to about 100 nanomolar, and calcium is present in a concentration of from about 0.5 to about 1.5 millimolar.

11. The composition according to claim 10, wherein the taxol is liposome-encapsulated.

12. The composition according to claim 10, wherein the taxol is present in the form of a physiologically-acceptable taxol derivative selected from the group consisting of taxol salts, taxol esters, taxol conjugates, and combinations thereof.

13. A composition for the ex vivo preservation and storage of organs intended for implantation into a subject requiring such implantation, the composition comprising:

a physiologically-acceptable ex vivo organ preservation solution having a solution osmolality of about 320 mOsm/liter and including taxol, calcium, and a lactobionate salt; and about 3 to 8 weight percent hydroxy ethyl starch having a molecular weight of from about 150,000 to about 350,000 Daltons, and wherein the starch is substantially free of ethylene glycol, ethylene chlorohydrin, sodium chloride, and acetone.

14. The composition according to claim 13, wherein the taxol is present in a concentration of from about 1 to about 100 nanomolar, and calcium is present in a concentration of from about 0.5 to about 1.5 millimolar.

15. The composition according to claim 14, further comprising potassium phosphate, glutathione, adenosine, glucose, N-2-hydroxyethylpiperazine-N'-2- ethanesulfonic acid buffer, magnesium gluconate, penicillin, insulin, dexamethasone.

16. The composition according to claim 13, including:

about 5 weight percent hydroxy ethyl starch having a molecular of from about 200,000 to about 300,000 Daltons, from about 1 to about 100 nM taxol, about 25 mM potassium phosphate, about 3 mM glutathione, about 5 mM adenosine, about 10 mM glucose, about 10 mM N-2-hydroxyethylpiperazine-N'-2-ethanesulfonic acid buffer, about 5 mM magnesium gluconate, about 1.5 mM calcium chloride, about 105 mM sodium gluconate, about 200,000 units penicillin, about 40 units insulin, and wherein the solution has a pH of from about 7.4 to about 7.5.

17. The composition according to claim 13, including:

about 5 weight percent hydroxy ethyl starch having a molecular of from about 200,000 to about 300,000 Daltons, from about 1 to about 100 nM taxol, about 25 mM potassium phosphate, about 3 mM glutathione, about 5 mM adenosine, about 100 mM potassium lactobionate, about 30 mM raffinose, about 5 mM magnesium sulfate, about 1.0 mM allopurinol, about 8mg/l dexamethasone, about 200,000 units penicillin, about 40 units insulin, and wherein the solution has a pH of from about 7.4 to about 7.5.

18. In a solution for the ex vivo preservation and storage of organs intended for implantation into a subject requiring such implantation, the improvement comprising:

adding taxol to the ex vivo organ preservation and storage solution.

19. The improvement according to claim 18, wherein the taxol is present in an amount ranging from about 1 to about 100 nM.

20. A cardioplegic composition, the composition comprising a physiologically-acceptable cardioplegic solution containing taxol.

21. The cardioplegic composition according to claim 20, wherein the taxol is present in a solution concentration of from about 1 to about 100 nanomolar.

* * * * *

UNITED STATES PATENT AND TRADEMARK OFFICE
CERTIFICATE OF CORRECTION

PATENT NO : 5,696,152
DATED : December 9, 1997
INVENTOR(S): James H. Southard

It is certified that error appears in the above-identified patent and that said Letters Patent is hereby corrected as shown below:

At column 1, in the space immediately following the Title of the Invention, please insert:

--This invention was made with United States government support awarded by NIH, grant # DK 35143. The United States Government has certain rights in this invention.--

Signed and Sealed this

Twenty-fourth Day of February, 1998

*Attest:*

BRUCE LEHMAN

*Attesting Officer*  *Commissioner of Patents and Trademarks*